United States Patent
Hatanaka et al.

(10) Patent No.: US 10,603,250 B2
(45) Date of Patent: Mar. 31, 2020

(54) ONE-PACK TYPE DENTINAL TUBULE OCCLUSION MATERIAL

(71) Applicant: KURARAY NORITAKE DENTAL INC., Kurashiki-shi (JP)

(72) Inventors: Kenji Hatanaka, Tainai (JP); Shumei Ishihara, Tainai (JP)

(73) Assignee: KURARAY NORITAKE DENTAL INC., Karashiki-shi (JP)

( * ) Notice: Subject to any disclaimer, the term of this patent is extended or adjusted under 35 U.S.C. 154(b) by 291 days.

(21) Appl. No.: 15/522,434

(22) PCT Filed: Oct. 29, 2015

(86) PCT No.: PCT/JP2015/005453
§ 371 (c)(1),
(2) Date: Apr. 27, 2017

(87) PCT Pub. No.: WO2016/067622
PCT Pub. Date: May 6, 2016

(65) Prior Publication Data
US 2017/0333295 A1    Nov. 23, 2017

(30) Foreign Application Priority Data

Oct. 30, 2014    (JP) .................................. 2014-221271

(51) Int. Cl.
| | |
|---|---|
| A61K 6/033 | (2006.01) |
| A61K 6/06 | (2006.01) |
| A61Q 11/00 | (2006.01) |
| A61K 8/24 | (2006.01) |
| A61K 6/00 | (2020.01) |

(52) U.S. Cl.
CPC ............ *A61K 6/033* (2013.01); *A61K 6/0008* (2013.01); *A61K 6/0643* (2013.01); *A61K 8/24* (2013.01); *A61Q 11/00* (2013.01)

(58) Field of Classification Search
CPC ..... A61K 6/033; A61K 6/0008; A61K 6/0643
See application file for complete search history.

(56) References Cited

U.S. PATENT DOCUMENTS

| | | | |
|---|---|---|---|
| 4,612,053 A * | 9/1986 | Brown ................ | A61K 8/24 106/35 |
| 5,525,148 A | 6/1996 | Chow et al. | |
| 5,954,867 A | 9/1999 | Chow et al. | |
| 5,976,234 A | 11/1999 | Chow et al. | |
| 5,997,624 A | 12/1999 | Chow et al. | |
| 9,962,319 B2 * | 5/2018 | Ishihara ............... | A61K 6/0017 |
| 2007/0218017 A1 | 9/2007 | Busch et al. | |
| 2012/0027829 A1 | 2/2012 | Hashimoto et al. | |
| 2013/0108708 A1 | 5/2013 | Xu | |
| 2013/0189337 A1 | 7/2013 | Hashimoto et al. | |

FOREIGN PATENT DOCUMENTS

| | | |
|---|---|---|
| EP | 1 731 132 A1 | 12/2006 |
| JP | 10-17449 A | 1/1998 |
| JP | 10-504467 A | 5/1998 |
| JP | 2005-325102 A | 11/2005 |
| JP | 2007-190226 A | 8/2007 |
| JP | 2014-189540 A | 10/2014 |
| WO | 95/08319 A1 | 3/1995 |
| WO | 2010/113800 A1 | 10/2010 |
| WO | 2012/046667 A1 | 4/2012 |

OTHER PUBLICATIONS

D.H. Pashley, et al., "The Effects of Calcium Hydroxide on Dentin Permeability", Journal of Dental Research, vol. 65, No. 3, p. 417-420, (Mar. 1986).

Kelvin C.Y. Tay, et al., "In Vitro Evaluation of a Ceramicrete-based Root-end Filling Material", Journal of Endodontics, vol. 33, No. 12, pp. 1438-1443, (Dec. 2007).

International Search Report dated Feb. 2, 2016 in PCT/JP2015/005453 Filed Oct. 29, 2015.

Extended European Search Report dated Jun. 6, 2018 in Patent Application No. 15854470.0, 7 pages.

* cited by examiner

*Primary Examiner* — C Melissa Koslow

(74) *Attorney, Agent, or Firm* — Oblon, McClelland, Maier & Neustadt, L.L.P.

(57) ABSTRACT

The present invention provides a dentinal tubule occlusion material excellent in terms of initial degree of dentinal tubule occlusion, resistance of dentinal tubule occlusion to acids, handling properties, and storage stability. The present invention relates to an one-pack type dentinal tubule occlusion material comprising fluorapatite particles (A) having an average particle diameter of 0.6 to 10 μm, inorganic particles (B) having an average particle diameter of 0.6 to 10 μm and reactive with water to form apatite, and a non-aqueous dispersant (C).

5 Claims, No Drawings

ONE-PACK TYPE DENTINAL TUBULE OCCLUSION MATERIAL

TECHNICAL FIELD

The present invention relates to a dentinal tubule occlusion material that is superior to conventional dentinal tubule occlusion materials in terms of initial degree of dentinal tubule occlusion, resistance of dentinal tubule occlusion to acids, handling properties, and storage stability.

BACKGROUND ART

Biting or drinking something cold, hot, sweet, or sour may elicit a sharp, lancinating pain in a tooth, and such a pain is believed to arise from a stimulus to the dentinal nerves of the tooth. A huge number of dentinal tubules extend through tooth dentin, and the interior of the dentinal tubules is full of tissue fluid. A tooth with exposed dentin is thought to experience pain as follows: An external stimulus forces the tissue fluid in the dentinal tubules to move and consequently stimulate sensory nerves in the vicinity of the boundary between the dental pulp and dentin. Such a stimulus can be caused by anything that can cause movement of the tissue fluid in the dentinal tubules. This means that dentinal pain can be elicited by any of mechanical or thermal stimuli, sweetness, sourness, and stimuli that induce a change in osmotic pressure. The pain therefore occurs, for example, during eating, drinking, brushing with a toothbrush, and exercise, thus significantly affecting the daily life. The types of dentinal hypersensitivity include: cervical hypersensitivity associated with defective enamel or cementum resulting from causes such as dental caries and tooth abrasion due to improper brushing with a toothbrush; and root hypersensitivity associated with phenomena such as gingival recession due to improper brushing. In recent years, the population is increasingly aging and storage of vital teeth is attracting a growing attention. This produces an increasing trend in the prevalence of dentinal hypersensitivity attributed to gingival recession or root exposure.

Most of treatment techniques currently employed against dentinal hypersensitivity are intended to inhibit the movement of the tissue fluid in the dentinal tubules. Examples of techniques for blocking external stimuli with the use of various materials include: (1) mechanical covering of exposed dentin surface with a resin material or glass ionomer cement; (2) occlusion of tubules with a reaction product of oxalic acid with calcium contained in dentin; and (3) occlusion of tubules with intratubular protein coagulated by glutaraldehyde.

The above conventional techniques, however, have a disadvantage in that the materials used have a low pH or in that the materials are highly toxic and are not safe to use for treating subgingival areas or interdental areas. In addition, dentinal tubule occlusion accomplished by the conventional techniques unfortunately fails to remain intact and maintain its effect in an oral environment. To solve these problems, the following techniques using calcium phosphate have recently been disclosed.

Patent Literature 1 describes a composition for use against dentinal hypersensitivity that is capable of prevention and treatment of dentinal hypersensitivity, the composition including particles of hydroxyapatite or tricalcium phosphate that have a particle diameter of 1.0 μm to 5.0 μm. However, unfortunately, this composition is incapable of achieving secure occlusion of dentinal tubules, due to lacking inorganic particles (B) having an average particle diameter of 0.6 to 10 μm and reactive with water to form apatite (the inorganic particles (B) are essential for the present invention), and fails to achieve durable dentinal tubule occlusion.

Patent Literature 2 describes a dentinal tubule occlusion material that is characterized by containing calcium phosphate particles not larger than 900 nm. This literature alleges that the material can reliably fill the interior of dentinal tubules and that the calcium phosphate particles filling the interior of the dentinal tubules can act as cores to promote remineralization. However, with the mere use of small calcium phosphate particles not larger than 900 nm, dissolution of particles with a large specific surface area proceeds more readily than mineralization in the oral environment, which leads not only to failure of secure initial physical occlusion but also to post-occlusion detachment of the occlusion product due to physical stimuli such as those given by gargling, eating, and drinking. Furthermore, the dentinal tubule occlusion material is neither capable of achieving secure occlusion of dentinal tubules nor capable of achieving durable dentinal tubule occlusion.

Patent Literature 3 describes a two-pack type dentinal tubule occlusion material that is characterized by including a component containing tetracalcium phosphate particles and an alkali metal phosphate and a component containing water and by undergoing conversion to hydroxyapatite as a result of mixing of the two components. This occlusion material is capable of depositing hydroxyapatite deep into dentinal tubules and achieving secure occlusion of the dentinal tubules. However, such a two-pack type material requires the practitioner to perform material preparation each time he/she uses it. If provided in the form of an one-pack type material, the occlusion material is unsatisfactory in terms of storage stability or resistance of dentinal tubule occlusion to acids.

Patent Literature 4 describes a two-pack type dentinal tubule occlusion material that includes a component containing poorly-soluble calcium phosphate particles and a phosphorus-free calcium compound and a component containing water and that undergoes gradual conversion to hydroxyapatite as a result of mixing of the two components. This occlusion material is excellent in terms of initial degree of dentinal tubule occlusion and durability of dentinal tubule occlusion. However, such a two-pack type material requires the practitioner to perform material preparation each time he/she uses it. If provided in the form of an one-pack type material, the occlusion material is unsatisfactory in terms of storage stability or resistance of dentinal tubule occlusion to acids.

That is, conventional dentinal tubule occlusion materials as disclosed in Patent Literatures mentioned above are those which cannot provide a sufficient initial degree of dentinal tubule occlusion, those which have a disadvantage in terms of durability of dentinal tubule occlusion, those which require material preparation each time they are used, or those which, when provided in the form of an one-pack type material, are unsatisfactory in terms of storage stability or resistance of dentinal tubule occlusion to acids.

CITATION LIST

Patent Literature

Patent Literature 1: JP 10-17449 A
Patent Literature 2: JP 2005-325102 A
Patent Literature 3: WO 2010/113800 A1
Patent Literature 4: WO 2012/046667 A1

SUMMARY OF INVENTION

Technical Problem

The present invention has been made to solve the above problems and has as its object to provide a dentinal tubule occlusion material that is excellent in terms of initial degree of dentinal tubule occlusion, resistance of dentinal tubule occlusion to acids, handling properties, and storage stability.

Solution to Problem

The above problems can be solved by providing an one-pack type dentinal tubule occlusion material comprising: fluorapatite particles (A) having an average particle diameter of 0.6 to 10 μm; inorganic particles (B) having an average particle diameter of 0.6 to 10 μm and reactive with water to form apatite; and a non-aqueous dispersant (C).

In the present invention, it is preferable that a weight ratio (A/B) of the fluorapatite particles (A) to the inorganic particles (B) be 0.1 to 50.

In the present invention, it is preferable that the non-aqueous dispersant (C) be comprised in an amount of 25 to 900 parts by weight relative to 100 parts by weight of the total of the fluorapatite particles (A) and the inorganic particles (B).

In the present invention, it is preferable that the inorganic particles (B) comprise a mixture of basic calcium phosphate particles (b1) and poorly-soluble calcium phosphate particles (b2) or a mixture of the poorly-soluble calcium phosphate particles (b2) and a phosphorus-free calcium compound (b3), and that a Ca/P ratio in the total of the particles (b1) and the particles (b2) or in the total of the particles (b2) and the compound (b3) be 1.2 to 2.0.

In the present invention, it is preferable that the inorganic particles (B) comprise a mixture of basic calcium phosphate particles (b1), poorly-soluble calcium phosphate particles (b2), and a phosphorus-free calcium compound (b3), and that a Ca/P ratio in the total of the particles (b1), the particles (b2), and the compound (b3) be 1.5 to 3.0.

In the present invention, it is preferable that the non-aqueous dispersant (C) be at least one selected from the group consisting of a polyether, a monohydric alcohol, and a polyhydric alcohol.

Advantageous Effects of Invention

The present invention provides a dentinal tubule occlusion material that is excellent in terms of initial degree of dentinal tubule occlusion, resistance of dentinal tubule occlusion to acids, handling properties, and storage stability. In particular, the excellent storage stability eliminates the need for material preparation in clinical practice; that is, the dentinal tubule occlusion material can be used in the form of an one-pack type dentinal tubule occlusion material. Furthermore, the excellent resistance to acids provides increased retention of the therapeutic effect.

DESCRIPTION OF EMBODIMENTS

The dentinal tubule occlusion material of the present invention comprises fluorapatite particles (A) having an average particle diameter of 0.6 to 10 μm, inorganic particles (B) having an average particle diameter of 0.6 to 10 μm and reactive with water to form apatite, and a non-aqueous dispersant (C). The present inventors have discovered that when the fluorapatite particles (A) having an average particle diameter of 0.6 to 10 μm and the inorganic particles (B) having an average particle diameter of 0.6 to 10 μm and reactive with water to form apatite are mixed with the non-aqueous dispersant (C), the initial degree of dentinal tubule occlusion and the resistance of dentinal tubule occlusion to acids can be maintained. The following will describe a possible mechanism of action, although no definite mechanism has been clarified.

The fluorapatite ($Ca_{10}(PO_4)_6F_2$) particles (A) and the inorganic particles (B) are thought to be capable of physically penetrating into dentinal tubules to a depth of several micrometers from the tooth structure surface immediately after dentinal tubule occlusion treatment and occupying most of the volume of the tubules. After penetrating into the dentinal tubules, the inorganic particles (B) contact with saliva or water in the oral cavity to form dense apatite, providing a further increase in the degree of dentinal tubule occlusion. The apatite formed seems to act as a crystal growth core for mineralization of the walls of the dentinal tubules and the peripheral dentin and finally merge into dentin. The resulting tubule occlusion product seems, when subjected to "intrapulpal pressure" produced by the intrapulpal fluid flowing out of the dental pulp toward the tooth structure surface, to undergo further mineralization by means of the intrapulpal fluid rather than being broken or detached by the pressure. Presumably in this way, the fluorapatite particles (A) and inorganic particles (B) of the present invention can achieve physical occlusion of the dentinal tubules in the dentin surface efficiently, in addition to which the inorganic particles (B) can react with saliva or water in the oral cavity to form apatite that ensures secure occlusion of the dentinal tubules. The resulting dentinal tubule occlusion product, which contains the fluorapatite particles (A) having high acid resistance, is capable of exhibiting high acid resistance and therefore increased retention of the therapeutic effect.

The fluorapatite particles (A) used in the dentinal tubule occlusion material of the present invention have an average particle diameter of 0.6 to 10 μm. When the average particle diameter of the fluorapatite particles (A) is 0.6 μm or more, more efficient occlusion of dentinal tubules and a higher initial degree of dentinal tubule occlusion are achieved compared to when the average particle diameter is less than 0.6 μm. The average particle diameter is therefore 0.6 μm or more, preferably 1.0 μm or more, and more preferably 1.5 μm or more. In addition, the fluorapatite particles (A) can more readily penetrate into dentinal tubules when the average particle diameter is 10 μm or less than when the average particle diameter is more than 10 μm. The average particle diameter is therefore 10 μm or less, preferably 8.0 μm or less, and more preferably 6.0 μm or less. The average particle diameter of the fluorapatite particles (A) used in the present invention is determined herein by measurement and calculation based on a laser diffraction-scattering method using a laser diffraction particle size analyzer.

The fluorapatite particles (A) used in the present invention have high acid resistance. Thus, the occlusion product formed in dentinal tubules, which contains the fluorapatite particles (A), is capable of exhibiting high acid resistance and therefore increased retention of the therapeutic effect.

The method for producing the fluorapatite particles (A) used in the present invention is not particularly limited. When a commercialized product is available, the commercialized product can be used per se. Alternatively, the commercialized product may be further ground and then used. In this case, a grinder such as a jet mill, ball mill, or grinding mixer can be used. Alternatively, the fluorapatite particles (A) may be obtained by grinding fluorapatite particles (A) together with a liquid medium such as an alcohol using a grinding mixer, ball mill or the like to prepare a slurry and then by drying the prepared slurry. Preferred as the grinder used in this case is a ball mill. As the materials of the pot and balls of the mill there are preferably used alumina and zirconia.

The inorganic particles (B) used in the dentinal tubule occlusion material of the present invention have an average particle diameter of 0.6 to 10 μm and are reactive with water to form apatite. The inorganic particles (B) of the present invention are capable of reacting with water to form hydroxyapatite ($Ca_{10}(PO_4)_6(OH)_2$, which may hereinafter be abbreviated as "Hap") and thereby achieving secure occlusion of dentinal tubules. If the average particle diameter of the inorganic particles (B) is less than 0.6 μm, this may lead to a failure of efficient occlusion of dentinal tubules or to a decrease in the initial degree of dentinal tubule occlusion. Thus, the average particle diameter is preferably 1.0 μm or more and more preferably 1.5 μm or more. If the average particle diameter of the inorganic particles (B) is more than 10 μm, the particles may fail to penetrate into dentinal tubules. Thus, the average particle diameter is preferably 8.0 μm or less and more preferably 6.0 μm or less. The average particle diameter of the inorganic particles (B) used in the present invention is determined herein by measurement and calculation based on a laser diffraction-scattering method using a laser diffraction particle size analyzer.

The laser diffraction-scattering method can be carried out, for example, using a laser diffraction particle size analyzer (SALD-2100, manufactured by Shimadzu Corporation) and using a 0.2% aqueous solution of sodium hexametaphosphate as a dispersion medium.

The inorganic particles (B) used in the present invention, which have an average particle diameter of 0.6 to 10 μm and are reactive with water to form apatite, are not particularly limited, as long as they contribute to the effect of the present invention. Phosphate ions and calcium ions are necessary for formation of hydroxyapatite by reaction with a watery substance such as saliva. Thus, the following are used for the inorganic particles (B): a mixture of calcium phosphate compounds capable of producing phosphate ions and calcium ions; a mixture of a calcium phosphate compound and a phosphorus-free calcium compound; and a combination of these mixtures. It is preferable for the inorganic particles (B) to comprise, for example, a mixture of basic calcium phosphate particles (b1) and poorly-soluble calcium phosphate particles (b2), a mixture of the poorly-soluble calcium phosphate particles (b2) and a phosphorus-free calcium compound (b3), or a mixture of the basic calcium phosphate particles (b1), the poorly-soluble calcium phosphate particles (b2), and the phosphorus-free calcium compound (b3). In terms of initial degree of dentinal tubule occlusion and resistance of dentinal tubule occlusion to acids, it is most preferable for the inorganic particles (B) to comprise a mixture of the basic calcium phosphate particles (b1), the poorly-soluble calcium phosphate particles (b2), and the phosphorus-free calcium compound (b3).

The basic calcium phosphate particles (b1) used in the present invention preferably include, but are not limited to, particles of at least one selected from the group consisting of tetracalcium phosphate ($Ca_4(PO_4)_2O$, which may hereinafter be abbreviated as "TTCP") and octacalcium phosphate pentahydrate ($Ca_8H_2(PO_4)_6 \cdot 5H_2O$). Among these particles, the tetracalcium phosphate ($Ca_4(PO_4)_2O$) particles are more preferred, particularly in terms of initial degree of dentinal tubule occlusion and resistance of dentinal tubule occlusion to acids.

The poorly-soluble calcium phosphate particles (b2) used in the present invention preferably include, but are not limited to, particles of at least one selected from the group consisting of dibasic calcium phosphate anhydrous ($CaHPO_4$, which may hereinafter be abbreviated as "DCPA"), tricalcium phosphate ($Ca_3(PO_4)_2$, which may hereinafter be abbreviated as "TCP"), monobasic calcium phosphate anhydrous ($Ca(H_2PO_4)_2$), amorphous calcium phosphate ($Ca_3(PO_4)_2 \cdot xH_2O$), calcium acid pyrophosphate ($CaH_2P_2O_7$), dibasic calcium phosphate dihydrate ($CaHPO_4 \cdot 2H_2O$, which may hereinafter be abbreviated as "DCPD"), and monobasic calcium phosphate monohydrate ($Ca(H_2PO_4)_2 \cdot H_2O$). Among these particles, particles of at least one selected from the group consisting of dibasic calcium phosphate anhydrous ($CaHPO_4$), tricalcium phosphate ($Ca_3(PO_4)_2$), dibasic calcium phosphate dihydrate ($CaHPO_4 \cdot 2H_2O$), and monobasic calcium phosphate anhydrous ($Ca(H_2PO_4)_2$) are more preferred. In particular, in terms of initial degree of dentinal tubule occlusion and resistance of dentinal tubule occlusion to acids, particles of at least one selected from the group consisting of dibasic calcium phosphate anhydrous ($CaHPO_4$), tricalcium phosphate ($Ca_3(PO_4)_2$), and dibasic calcium phosphate dihydrate ($CaHPO_4 \cdot 2H_2O$) are even more preferred.

The phosphorus-free calcium compound (b3) used in the present invention is preferably, but not limited to, at least one selected from the group consisting of calcium hydroxide ($Ca(OH)_2$), calcium oxide (CaO), calcium chloride ($CaCl_2$), calcium nitrate ($Ca(NO_3)_2 \cdot nH_2O$), calcium acetate ($Ca(CH_3CO_2)_2 \cdot nH_2O$), calcium lactate ($C_6H_{10}CaO_6$), calcium citrate ($Ca_3(C_6H_5O_7)_2 \cdot nH_2O$), calcium metasilicate ($CaSiO_3$), dicalcium silicate ($Ca_2SiO_4$), tricalcium silicate ($Ca_3SiO_5$), and calcium carbonate ($CaCO_3$). Among these, at least one selected from the group consisting of calcium hydroxide, calcium carbonate, calcium metasilicate, dicalcium silicate, and tricalcium silicate is more preferred in terms of initial degree of dentinal tubule occlusion and resistance of dentinal tubule occlusion to acids, and calcium carbonate is even more preferred.

The methods for producing the basic calcium phosphate particles (b1), poorly-soluble calcium phosphate particles (b2), and phosphorus-free calcium compound (b3) used as the inorganic particles (B) in the present invention are not particularly limited. When a commercialized product is available, the commercialized product can be used per se. Alternatively, the commercialized product may be further ground and then used. In this case, a grinder such as a jet mill, ball mill, or grinding mixer can be used. Alternatively, the inorganic particles (B) may be obtained by grinding inorganic particles together with a liquid medium such as an alcohol using a grinding mixer, ball mill or the like to prepare a slurry and then by drying the prepared slurry. Preferred as the grinder used in this case is a ball mill. As the materials of the pot and balls of the mill there are preferably used alumina and zirconia.

In the present invention, when the inorganic particles (B) comprise a mixture of the basic calcium phosphate particles (b1) and the poorly-soluble calcium phosphate particles (b2) or a mixture of the poorly-soluble calcium phosphate particles (b2) and the phosphorus-free calcium compound (b3), the Ca/P ratio in the total of the particles (b1) and the particles (b2) or in the total of the particles (b2) and the compound (b3) is preferably 1.2 to 2.0, more preferably 1.3 to 1.9, and even more preferably 1.4 to 1.8. When the inorganic particles (B) comprise a mixture of the basic calcium phosphate particles (b1), the poorly-soluble calcium phosphate particles (b2), and the phosphorus-free calcium compound (b3), the Ca/P ratio in the total of the particles (b1), the particles (b2), and the compound (b3) is preferably 1.5 to 3.0, more preferably 1.6 to 2.9, and even more preferably 1.7 to 2.8. This can result in the one-pack type dentinal tubule occlusion material of the present invention that is excellent in terms of initial degree of dentinal tubule occlusion and resistance of dentinal tubule occlusion to acids.

Examples of the non-aqueous dispersant (C) used in the present invention include, but are not limited to: polyethers such as polyethylene glycol and polypropylene glycol; monohydric alcohols such as ethanol and methanol; and polyhydric alcohols such as glycerin, ethylene glycol, propylene glycol, and diglycerin. These may be used alone or in combination with one another. Among these, at least one selected from the group consisting of the polyethers, monohydric alcohols, and polyhydric alcohols is preferred. In particular, in terms of handling properties, at least one selected from the group consisting of the polyethers and polyhydric alcohols is more preferred, and at least one selected from the group consisting of glycerin, propylene glycol, and polyethylene glycol is even more preferred.

In the dentinal tubule occlusion material of the present invention, the weight ratio (A/B) of the fluorapatite particles (A) to the inorganic particles (B) is preferably 0.1 to 50. When the weight ratio is in this range, the fluorapatite particles (A) filling the interior of dentinal tubules can contribute to the increase in resistance of dentinal tubule occlusion to acids and, in addition, the inorganic particles (B) successfully close the gaps between the fluorapatite particles (A) to provide increased initial degree of dentinal tubule occlusion. To further enhance the above effect, the weight ratio (A/B) is more preferably 0.3 or more, even more preferably 0.5 or more, and particularly preferably 1.0 or more. To further enhance the above effect, the weight ratio (A/B) is more preferably 40 or less, even more preferably 30 or less, and particularly preferably 25 or less.

It is preferable for the dentinal tubule occlusion material of the present invention to comprise the non-aqueous dispersant (C) in an amount of 25 to 900 parts by weight relative to 100 parts by weight of the total of the fluorapatite particles (A) and the inorganic particles (B). If the content of the non-aqueous dispersant (C) is less than 25 parts by weight, formation of a paste may fail. The content is preferably 30 parts by weight or more and more preferably 35 parts by weight or more. If the content of the non-aqueous dispersant (C) is more than 900 parts by weight, satisfactory occlusion of dentinal tubules may not be achieved. The content is preferably 750 parts by weight or less and more preferably 500 parts by weight or less.

The dentinal tubule occlusion material of the present invention may comprise a fluorine compound if desired. In this case, the inorganic particles (B) having penetrated into dentinal tubules contact with saliva or water in the oral cavity to form dense fluorapatite, thereby providing an increase in the acid resistance of the resulting occlusion product. Examples of the fluorine compound to be used in the present invention include, but are not limited to, sodium fluoride, potassium fluoride, ammonium fluoride, lithium fluoride, cesium fluoride, magnesium fluoride, calcium fluoride, strontium fluoride, barium fluoride, copper fluoride, zirconium fluoride, aluminum fluoride, tin fluoride, sodium monofluorophosphate, potassium monofluorophosphate, hydrofluoric acid, sodium titanium fluoride, potassium titanium fluoride, hexylamine hydrofluoride, laurylamine hydrofluoride, glycine hydrofluoride, alanine hydrofluoride, fluorosilanes, and silver diamine fluoride. These may be used alone or in combination with one another. Among these, sodium fluoride, sodium monofluorophosphate, and tin fluoride are preferably used in terms of safety.

The content of the fluorine compound used in the present invention is not particularly limited. The content of the fluorine compound, calculated as fluoride ions, is preferably 0.01 to 10 parts by weight relative to 100 parts by weight of the total amount of the dentinal tubule occlusion material. To further increase the acid resistance of the resulting occlusion product, the content of the fluorine compound, calculated as fluoride ions, is more preferably 0.05 parts by weight or more relative to 100 parts by weight of the total amount of the dentinal tubule occlusion material. In terms of safety, the content of the fluorine compound, calculated as fluoride ions, is more preferably 5 parts by weight or less relative to 100 parts by weight of the total amount of the dentinal tubule occlusion material.

The dentinal tubule occlusion material of the present invention may further comprise other inorganic particles if desired. Examples of the other inorganic particles include, but are not limited to, particles of quartz, silica, alumina, zirconia, titania, silica-titania, silica-titania-barium oxide, silica-zirconia, silica-alumina, lanthanum glass, borosilicate glass, soda glass, barium glass, strontium glass, glass ceramic, aluminosilicate glass, barium boroaluminosilicate glass, strontium boroaluminosilicate glass, fluoroaluminosilicate glass, calcium fluoroaluminosilicate glass, strontium fluoroaluminosilicate glass, barium fluoroaluminosilicate glass, and strontium calcium fluoroaluminosilicate glass. These may be used alone or in combination with one another. Among these, at least one selected from the group consisting of barium glass, fluoroaluminosilicate glass, silica, and zirconia is preferred.

The dentinal tubule occlusion material of the present invention may comprise a thickener if desired. The incorporation of a thickener is intended to control the viscosity of the resulting paste and give the paste good properties that allow the practitioner to easily handle the paste. Examples of the thickener include: fumed silica; synthetic polymers such as polyvinyl alcohol, polyacrylic acid, polystyrene sulfonic acid, and polystyrene sulfonates; polyamino acids and salts thereof such as polyglutamic acid, polyglutamates, polyaspartic acid, polyaspartates, poly-L-lysine, and poly-L-lysine salts; cellulose compounds such as carboxymethyl cellulose, sodium carboxymethyl cellulose, hydroxypropyl cellulose, and hydroxypropyl methylcellulose; polysaccharides other than cellulose such as starches (e.g., starches having an amylose content of 10 to 70% such as corn starch, potato starch, and tapioca starch), dextran, alginic acid, alginates, carrageenan, guar gum, xanthan gum, cellulose gum, hyaluronic acid, hyaluronates, pectin, pectates, chitin, and chitosan; esters of acidic polysaccharides such as propylene glycol alginate; collagen; gelatin; and derivatives thereof. These may be used alone or in combination with one another. Fumed silica is particularly preferred, since the use of fumed silica makes it easy to give the resulting paste the desired properties.

The content of the thickener used in the present invention is preferably, but not limited to, 0.01 to 10 parts by weight relative to 100 parts by weight of the total amount of the dentinal tubule occlusion material. It is more preferable that the content of the thickener be 0.05 parts by weight or more relative to 100 parts by weight of the total amount of the dentinal tubule occlusion material, because in this case the resulting paste can have an increased flowability and therefore further improved handling properties. It is more preferable that the content of the thickener be 8 parts by weight or less relative to 100 parts by weight of the total amount of the dentinal tubule occlusion material, because in this case a decrease in the flowability of the paste can be prevented.

The dentinal tubule occlusion material of the present invention can incorporate any pharmacologically-acceptable substance if desired. Examples of such a substance that can be incorporated include: antibacterial agents such as cetylpyridinium chloride, sodium benzoate, methylparaben, paraoxybenzoic acid esters, and alkyldiaminoethylglycine hydrochloride; disinfectants; anticancer agents; antibiotic substances; blood circulation improving drugs such as actosin and PEG1; growth factors such as bFGF, PDGF, and BMP; cells that promote hard tissue formation, such as osteoblast cells, odontoblast cells, undifferentiated marrow-derived stem cells, embryonic stem (ES) cells, induced pluripotent stem (iPS) cells prepared by dedifferentiation of differentiated cells such as differentiated fibroblast cells through gene transfer, and cells prepared by differentiating those cells.

The dentinal tubule occlusion material of the present invention can incorporate a sweetener if desired. Examples of the sweetener include: natural sweeteners such as stevioside and glycyrrhiza extract; sugar alcohols such as maltitol, xylitol, sorbitol, mannitol, and erythritol; and artificial sweeteners such as aspartame, acesulfame potassium, sucralose, saccharin, and sodium saccharin. These may be used alone or in combination with one another.

The dentinal tubule occlusion material of the present invention can incorporate a flavor if desired. Examples of the flavor include menthol, orange oil, spearmint oil, peppermint oil, lemon oil, eucalyptus oil, and methyl salicylate. These may be used alone or in combination with one another.

The dentinal tubule occlusion material of the present invention is excellent in terms of initial degree of dentinal tubule occlusion, resistance of dentinal tubule occlusion to acids, handling properties, and storage stability. In particular, the excellent storage stability eliminates the need for material preparation in clinical practice; that is, the dentinal tubule occlusion material can be used in the form of an one-pack type non-aqueous dentinal tubule occlusion material. Furthermore, the excellent resistance to acids provides increased retention of the therapeutic effect.

In the present invention, the initial degree of dentinal tubule occlusion is evaluated by an initial value of dentin permeability reduction ratio described below in EXAMPLES. For the non-aqueous dentinal tubule occlusion material of the present invention, the initial value of dentin permeability reduction ratio is preferably 80% or more, more preferably 85% or more, even more preferably 87% or more, and particularly preferably 90% or more. The method for measuring the initial value of dentin permeability reduction ratio is as described below in EXAMPLES.

For the non-aqueous dentinal tubule occlusion material of the present invention, a post-acid immersion value of dentin permeability reduction ratio is preferably 70% or more, more preferably 75% or more, even more preferably 77% or more, and particularly preferably 80% or more. The method for measuring the post-acid immersion value of dentin permeability reduction ratio is as described below in EXAMPLES.

In the present invention, the resistance of dentinal tubule occlusion to acids is evaluated by a decrease in dentin permeability reduction ratio caused by acid immersion described below in EXAMPLES. For the non-aqueous dentinal tubule occlusion material of the present invention, the decrease in dentin permeability reduction ratio caused by acid immersion is preferably 10.0% or less, more preferably 8.0% or less, even more preferably 6.0% or less, and particularly preferably 5.0% or less. The method for measuring the decrease in dentin permeability reduction ratio caused by acid immersion is as described below in EXAMPLES.

The present invention encompasses embodiments obtainable by combining the above features in various manners within the technical scope of the present invention as long as the embodiments have the effect of the present invention.

EXAMPLES

Hereinafter, the present invention will be described in detail by examples. It should be noted that the present invention is not limited in any respect by the following examples and many modifications can be made by those of ordinary skill in the art within the technical concept of the present invention.

Average particle diameter measurement of the fluorapatite particles (A) and inorganic particles (B) used in the examples herein was performed using a laser diffraction particle size analyzer ("SALD-2100" manufactured by Shimadzu Corporation). The median diameter as calculated from the measurement result was employed as the average particle diameter.

[Preparation of Fluorapatite Particles (A)]

Fluorapatite Particles (A)-1: Average Particle Diameter 0.6 μm

Fluorapatite particles having an average particle diameter of 0.6 μm were obtained by processing commercially-available fluorapatite particles (manufactured by TAIHEI CHEMICAL INDUSTRIAL CO., LTD. and having an average particle diameter of 7.8 μm) four times using a jet mill (Nano Jetmizer NJ-100, manufactured by Aishin Nano Technologies CO., LTD.) under the following conditions: raw material supply pressure=0.7 MPa, grinding pressure=0.7 MPa, through put=8 kg/hr.

Fluorapatite Particles (A)-2: Average Particle Diameter 1.1 μm

Fluorapatite particles having an average particle diameter of 1.1 μm were obtained by processing commercially-available fluorapatite particles (manufactured by TAIHEI CHEMICAL INDUSTRIAL CO., LTD. and having an average particle diameter of 7.8 μm) two times using a jet mill (Nano Jetmizer NJ-100, manufactured by Aishin Nano Technologies CO., LTD.) under the following conditions: raw material supply pressure=0.7 MPa, grinding pressure=0.7 MPa, through put=8 kg/hr.

Fluorapatite Particles (A)-3: Average Particle Diameter 2.4 μm

Fluorapatite particles having an average particle diameter of 2.4 μm were obtained by processing commercially-available fluorapatite particles (manufactured by TAIHEI CHEMICAL INDUSTRIAL CO., LTD. and having an average particle diameter of 7.8 μm) once using a jet mill (Nano Jetmizer NJ-100, manufactured by Aishin Nano Technologies CO., LTD.) under the following conditions: raw material supply pressure=0.7 MPa, grinding pressure=0.7 MPa, through put=8 kg/hr.

Fluorapatite Particles (A)-4: Average Particle Diameter 7.8 μm

Commercially-available fluorapatite particles (manufactured by TAIHEI CHEMICAL INDUSTRIAL CO., LTD.) were used per se as fluorapatite particles having an average particle diameter of 7.8 μm.

[Preparation of Fluorapatite Particles (A″)]

Fluorapatite Particles (A′)-1: Average Particle Diameter 0.2 μm

Fluorapatite particles having an average particle diameter of 0.2 μm were obtained by processing commercially-available fluorapatite particles (manufactured by TAIHEI CHEMICAL INDUSTRIAL CO., LTD. and having an average particle diameter of 7.8 μm) five times using a jet mill (Nano Jetmizer NJ-100, manufactured by Aishin Nano Technologies CO., LTD.) under the following conditions: raw material supply pressure=0.7 MPa, grinding pressure=0.7 MPa, through put=8 kg/hr.

Fluorapatite Particles (A′)-2: Average Particle Diameter 20.4 μm

Commercially-available fluorapatite particles (manufactured by TAIHEI CHEMICAL INDUSTRIAL CO., LTD.) were used per se as fluorapatite particles having an average particle diameter of 20.4 μm.

[Preparation of Inorganic Particles (B)]

(1) Preparation of Basic Calcium Phosphate Particles (b1)

Tetracalcium phosphate (TTCP) particles: Average particle diameter 2.0 μm

Tetracalcium phosphate (TTCP) particles having an average particle diameter of 2.0 μm were obtained by processing commercially-available tetracalcium phosphate particles (manufactured by TAIHEI CHEMICAL INDUSTRIAL CO., LTD. and having an average particle diameter of 20.4 μm) five times using a jet mill (Nano Jetmizer NJ-100, manufactured by Aishin Nano Technologies CO., LTD.) under the following conditions: raw material supply pressure=0.7 MPa, grinding pressure=0.7 MPa, through put=8 kg/hr.

(2) Preparation of Poorly-Soluble Calcium Phosphate Particles (b2)

Dibasic calcium phosphate anhydrous (DCPA) particles and dibasic calcium phosphate dihydrate (DCPD) particles used in EXAMPLES were obtained by grinding commercially-available dibasic calcium phosphate anhydrous particles (complying with the Japanese Pharmacopoeia, manufactured by TAIHEI CHEMICAL INDUSTRIAL CO., LTD., and having an average particle diameter of 20.8 μm) and commercially-available dibasic calcium phosphate dihydrate particles (manufactured by TAIHEI CHEMICAL INDUSTRIAL CO., LTD. and having an average particle diameter of 23.2 μm), respectively, according to the methods described below.

Dibasic Calcium Phosphate Anhydrous Particles (b2)-1: Average Particle Diameter 0.6 μm Dibasic calcium phosphate anhydrous particles having an average particle diameter of 0.6 μm were obtained as follows: 50 g of commercially-available dibasic calcium phosphate anhydrous particles (complying with the Japanese Pharmacopoeia, manufactured by TAIHEI CHEMICAL INDUSTRIAL CO., LTD., and having an average particle diameter of 20.8 μm), 120 g of 95% ethanol ("Ethanol (95)" manufactured by Wako Pure Chemical Industries, Ltd.), and 240 g of zirconia balls having a diameter of 10 mm were placed in a 400 ml milling pot made of alumina ("Type A-3 HD pot mill" manufactured by Nikkato Corporation) and were wet-milled at a rotation speed of 120 rpm for 90 hours to obtain a slurry, from which ethanol was distilled off using a rotary evaporator and which was then dried at 60° C. for 6 hours and further vacuum-dried at 60° C. for 24 hours.

Dibasic Calcium Phosphate Anhydrous Particles (b2)-2: Average Particle Diameter 1.2 μm Dibasic calcium phosphate anhydrous particles having an average particle diameter of 1.2 μm were obtained as follows: 50 g of commercially-available dibasic calcium phosphate anhydrous particles (complying with the Japanese Pharmacopoeia, manufactured by TAIHEI CHEMICAL INDUSTRIAL CO., LTD., and having an average particle diameter of 20.8 μm), 120 g of 95% ethanol ("Ethanol (95)" manufactured by Wako Pure Chemical Industries, Ltd.), and 240 g of zirconia balls having a diameter of 10 mm were placed in a 400 ml milling pot made of alumina ("Type A-3 HD pot mill" manufactured by Nikkato Corporation) and were wet-milled at a rotation speed of 120 rpm for 48 hours to obtain a slurry, from which ethanol was distilled off using a rotary evaporator and which was then dried at 60° C. for 6 hours and further vacuum-dried at 60° C. for 24 hours.

Dibasic Calcium Phosphate Anhydrous Particles (b2)-3: Average Particle Diameter 2.0 μm Dibasic calcium phosphate anhydrous particles having an average particle diameter of 2.0 μm were obtained as follows: 50 g of commercially-available dibasic calcium phosphate anhydrous particles (complying with the Japanese Pharmacopoeia, manufactured by TAIHEI CHEMICAL INDUSTRIAL CO., LTD., and having an average particle diameter of 20.8 μm), 120 g of 95% ethanol ("Ethanol (95)" manufactured by Wako Pure Chemical Industries, Ltd.), and 240 g of zirconia balls having a diameter of 10 mm were placed in a 400 ml milling pot made of alumina ("Type A-3 HD pot mill" manufactured by Nikkato Corporation) and were wet-milled at a rotation speed of 120 rpm for 36 hours to obtain a slurry, from which ethanol was distilled off using a rotary evaporator and which was then dried at 60° C. for 6 hours and further vacuum-dried at 60° C. for 24 hours.

Dibasic Calcium Phosphate Anhydrous Particles (b2)-4: Average Particle Diameter 6.5 μm Dibasic calcium phosphate anhydrous particles having an average particle diameter of 6.5 μm were obtained as follows: 50 g of commercially-available dibasic calcium phosphate anhydrous particles (complying with the Japanese Pharmacopoeia, manufactured by TAIHEI CHEMICAL INDUSTRIAL CO., LTD., and having an average particle diameter of 20.8 μm), 120 g of 95% ethanol ("Ethanol (95)" manufactured by Wako Pure Chemical Industries, Ltd.), and 240 g of zirconia balls having a diameter of 10 mm were placed in a 400 ml milling pot made of alumina ("Type A-3 HD pot mill" manufactured by Nikkato Corporation) and were wet-milled at a rotation speed of 120 rpm for 20 hours to obtain a slurry, from which ethanol was distilled off using a rotary evaporator and which was then dried at 60° C. for 6 hours and further vacuum-dried at 60° C. for 24 hours.

Tricalcium Phosphate Particles (b2)-5: Average Particle Diameter 2.0 μm

Commercially-available α-tricalcium phosphate (manufactured by TAIHEI CHEMICAL INDUSTRIAL CO., LTD.) was used per se as tricalcium phosphate (α-TCP) particles having an average particle diameter of 2.0 μm.

Dibasic Calcium Phosphate Dihydrate Particles (b2)-6: Average Particle Diameter 2.3 μm Dibasic calcium phosphate dihydrate (DCPD) particles having an average particle diameter of 2.3 μm were obtained as follows: 50 g of commercially-available dibasic calcium phosphate dihydrate particles (manufactured by TAIHEI CHEMICAL INDUSTRIAL CO., LTD. and having an average particle diameter of 23.2 μm), 120 g of 95% ethanol ("Ethanol (95)" manufactured by Wako Pure Chemical Industries, Ltd.), and 240 g of zirconia balls having a diameter of 10 mm were placed in a 400 ml milling pot made of alumina ("Type A-3 HD pot mill" manufactured by Nikkato Corporation) and were wet-milled at a rotation speed of 120 rpm for 36 hours to obtain a slurry, from which ethanol was distilled off using a rotary evaporator and which was then dried at 60° C. for 6 hours and further vacuum-dried at 60° C. for 24 hours.

Tricalcium Phosphate Particles (b2)-7: Average Particle Diameter 2.5 μm

Commercially-available β-tricalcium phosphate (manufactured by TAIHEI CHEMICAL INDUSTRIAL CO., LTD.) was used per se as tricalcium phosphate (β-TCP) particles having an average particle diameter of 2.5 μm.

(3) Preparation of Phosphorus-Free Calcium Compound (b3)

Calcium carbonate particles (b3)-1: Average Particle Diameter 2.4 μm

Commercially-available calcium carbonate (light calcium carbonate, manufactured by Yabashi Industries Co., Ltd.) was used per se as calcium carbonate particles having an average particle diameter of 2.4 μm.

Calcium Hydroxide Particles (b3)-2: Average Particle Diameter 2.1 μm

Calcium hydroxide particles having an average particle diameter of 2.1 μm were obtained as follows: 50 g of commercially-available calcium hydroxide particles (manufactured by KAWAI LIME INDUSTRY CO., LTD. and having an average particle diameter of 14.5 μm), 240 g of 99.5% ethanol ("Ethanol, Dehydrated (99.5)" manufactured by Wako Pure Chemical Industries, Ltd.), and 480 g of zirconia balls having a diameter of 10 mm were placed in a 1000 ml milling pot made of alumina ("HD-B-104 pot mill" manufactured by Nikkato Corporation) and were wet-milled under vibration at a rotation speed of 1500 rpm for 7 hours to obtain a slurry, from which ethanol was distilled off using a rotary evaporator and which was then dried at 60° C. for 6 hours.

Tricalcium Silicate Particles (b3)-3: Average Particle Diameter 1.9 μm

Commercially-available tricalcium silicate (manufactured by Tomita Pharmaceutical Co., Ltd.) was used per se as tricalcium silicate particles having an average particle diameter of 1.9 μm.

Dicalcium Silicate Particles (b3)-4: Average Particle Diameter 2.5 μm

Commercially-available dicalcium silicate (manufactured by Tomita Pharmaceutical Co., Ltd.) was used per se as dicalcium silicate particles having an average particle diameter of 2.5 μm.

[Preparation of Inorganic Particles (B')]

(1) Basic Calcium Phosphate Particles (b1')

Tetracalcium Phosphate (TTCP) Particles: Average Particle Diameter 20.4 μm

Commercially-available tetracalcium phosphate particles (manufactured by TAIHEI CHEMICAL INDUSTRIAL CO., LTD.) were used per se as tetracalcium phosphate (TTCP) particles having an average particle diameter of 20.4 μm.

(2) Poorly-Soluble Calcium Phosphate Particles (b2')

Dibasic Calcium Phosphate Anhydrous Particles (b2'): Average Particle Diameter 20.8 μm Commercially-available dibasic calcium phosphate anhydrous particles (complying with the Japanese Pharmacopoeia, manufactured by TAIHEI CHEMICAL INDUSTRIAL CO., LTD., and having an average particle diameter of 20.8 μm) were used per se as dibasic calcium phosphate anhydrous (DCPA) particles (b2') in the comparative examples.

(3) Phosphorus-Free Calcium Compound (b3')

Calcium Hydroxide Particles (b3'): Average Particle Diameter 14.5 μm

Commercially-available calcium hydroxide particles (manufactured by KAWAI LIME INDUSTRY CO., LTD.) were used per se as calcium hydroxide particles (b3') having an average particle diameter of 14.5 μm.

[Preparation of Non-Aqueous Dispersant (C)]

Two commercially-available polyethylene glycols having different molecular weights (MACROGOL 400 and MACROGOL 4000, manufactured by Sanyo Chemical Industries, Ltd.) and a commercially-available glycerin (manufactured by Wako Pure Chemical Industries, Ltd.) were used per se.

[Preparation of Fluorine Compound]

Commercially-available sodium fluoride (sodium fluoride, manufactured by Wako Pure Chemical Industries, Ltd.) was used per se as sodium fluoride (NaF) incorporated as a fluorine compound.

[Preparation of Thickener]

Commercially-available fumed silica (Ar-380, manufactured by Nippon Aerosil Co., Ltd.) was used per se as fumed silica incorporated as a thickener.

[Preparation of Hydroxyapatite]

Commercially-available hydroxyapatite particles (SHAp, rod-shaped particles, manufactured by Sofsera Corporation) were used per se as hydroxyapatite particles (Hap) having an average particle diameter of 150 nm.

[Preparation of Alkali Metal Phosphate]

Dibasic sodium phosphate particles (having an average particle diameter of 5.2 μm) were used as an example of the alkali metal phosphate in Comparative Examples. The particles were obtained by processing commercially-available dibasic sodium phosphate (manufactured by Wako Pure Chemical Industries, Ltd.) once using a jet mill (Nano Jetmizer NJ-100, manufactured by Aishin Nano Technologies CO., LTD.) under the following conditions: raw material supply pressure=0.7 MPa, grinding pressure=0.7 MPa, through put=8 kg/hr.

[Preparation of Dentinal Tubule Occlusion Material]

Examples 1 to 32

In Examples 1 to 32, one-pack type dentinal tubule occlusion materials were prepared by weighing raw materials onto an agate mortar and mixing the raw materials using an agate pestle for 5 minutes; the preparation was done in such a manner that the dentinal tubule occlusion materials had the compositions shown in Tables 1 to 3 and had a total weight of 20 g. The average particle diameters of the fluorapatite particles (A), inorganic particles (B), etc remained substantially unchanged before and after the mixing.

Comparative Examples 1 to 7

In Comparative Examples 1 to 7, one-pack type dentinal tubule occlusion materials were prepared by weighing raw materials onto an agate mortar and mixing the raw materials using an agate pestle for 5 minutes; the preparation was done in such a manner that the dentinal tubule occlusion materials had the compositions shown in Table 4 and had a total weight of 20 g. The average particle diameters of the various particles remained substantially unchanged before and after the mixing.

Comparative Examples 8 and 9

A dentinal tubule occlusion material of Comparative Example 8 was prepared by mixing 1.2 g of a powder described below and 1.0 g of water for 30 seconds, and a dentinal tubule occlusion material of Comparative Example 9 was prepared by mixing 1.9 g of another powder described below and 1.0 g of water for 30 seconds. The preparation was done in such a manner that the pastes resulting from the mixing of the powders with water had the compositions shown in Table 4. The powder used in Comparative Example 8 was composed of tetracalcium phosphate, dibasic calcium phosphate anhydrous, and dibasic sodium phosphate. This powder was prepared by weighing these components onto an agate mortar and mixing them using an agate pestle for 5 minutes so that the powder had a total weight of 10 g. The powder used in Comparative Example 9 was composed of dibasic calcium phosphate anhydrous, calcium hydroxide, and dibasic sodium phosphate. This powder was prepared by weighing these components onto an agate mortar and mixing them using an agate pestle for 5 minutes so that the powder had a total weight of 10 g. The average particle diameters of the components remained substantially unchanged before and after the mixing.

[Evaluation of Handling Properties]

The handling properties of the dentinal tubule occlusion materials prepared as above were evaluated. The criteria for evaluation of the handling properties were as follows.

A: The material is a soft paste and is easy to rub into dentin in the form of a paste by the below-described method using a microbrush. The paste is easy to wash away with water.

B: The material is a relatively hard paste and can be rubbed into dentin in the form of a paste by the below-described method using a microbrush. The paste can be washed away with water.

C: The dentinal tubule occlusion material has a high viscosity and is difficult to rub into dentin in the form of a paste by the below-described method using a microbrush.

Pastes having properties rated as A or B are preferably used.

[Evaluation of Storage Stability]

Each of the dentinal tubule occlusion materials prepared as above was weighed to 5 g and put in a screw-cap glass vial, which was allowed to stand at 37° C. for 24 hours. The storage stability of the material was rated as "Poor" when the material was observed to cure in the screw-cap glass vial after 24 hours, while when the material remained in the form of a paste without curing, the storage stability was rated as "Good".

[Evaluation of Dentin Permeability Reduction Ratio]

(1) Preparation of Disc of Bovine Tooth for Evaluation of Dentin permeability Reduction Ratio A healthy bovine incisor was trimmed from its buccal dentin using a rotating grinder with #80 and #1000 abrasive paper to prepare a disc of bovine tooth having a diameter of about 1.5 cm and a thickness of 0.9 mm. The surface of this disc of bovine tooth was further ground with wrapping films (wrapping films #1200, #3000, and #8000, manufactured by Sumitomo 3M) so that the disc had a thickness of 0.7 mm and a smooth surface. This disc of bovine tooth was immersed in a five-fold diluted 0.5 M EDTA solution (manufactured by Wako Pure Chemical Industries, Ltd.) for 180 seconds and then washed in distilled water for about 30 seconds. The disc of bovine tooth for use in evaluation of the dentin permeability reduction ratio was thus prepared.

(2) Preparation of Artificial Saliva

Sodium chloride (8.77 g, 150 mmol), monobasic potassium phosphate (122 mg, 0.9 mmol), calcium chloride (166 mg, 1.5 mmol), and Hepes (4.77 g, 20 mmol) were each weighed into a weighing dish, and were sequentially added to about 800 ml of distilled water held in a 2000 ml beaker under stirring. After confirmation of complete dissolution of the solutes, a 10% aqueous sodium hydroxide solution was added dropwise with simultaneous measurement of the solution acidity by a pH meter (F55, manufactured by HORIBA, Ltd.) to adjust the pH to 7.0. The resulting solution was then placed in a 1000 ml measuring flask, in which the volume of the solution was adjusted to obtain 1000 ml of artificial saliva.

(3) Preparation of Sample for Evaluation of Dentin Permeability Reduction Ratio (Initial Value)

An amount of 0.1 g of a paste of each of the dentinal tubule occlusion materials having the compositions shown in Tables 1 to 4 was rubbed on the buccal dentin surface of the above disc of bovine tooth using Microbrush Superfine (an applicator manufactured by MICROBRUSH INTERNATIONAL and having a diameter of 1.0 mm) for 30 seconds to occlude dentinal tubules. After that, the paste remaining on the dentin surface was removed by distilled water, and the disc of bovine tooth was immersed in the artificial saliva prepared as above at 37° C. for 24 hours. In this manner, samples for evaluation of the dentin permeability reduction ratio (initial value) were prepared (n=5).

(4) Preparation of Sample for Evaluation of Dentin Permeability Reduction Ratio (Post-Acid Immersion Value)

The samples (n=5) having undergone the evaluation of dentin permeability reduction ratio (initial value) were each horizontally immersed in 30 ml of a 0.1 M lactate-buffered solution (pH=4.75) held in a vessel at 37° C. for 10 minutes, with the surface treated with the dentinal tubule occlusion material facing upward. After that, the disc of bovine tooth was washed with distilled water, and then immersed in the artificial saliva at 37° C. The series of the immersion in the acid solution and the immersion in the artificial saliva was defined as one cycle of acid immersion. This cycle of acid immersion was repeated for 14 days at a frequency of once per day (at intervals of 24 hours). In this manner, samples for evaluation of the dentin permeability reduction ratio (post-acid immersion value) were prepared (n=5).

(5) Dentin Permeability Reduction Ratio (Initial Value)

The measurement of the dentin permeability reduction ratio was performed according to a method of Pashley et al. (D. H. Pashley et al., Journal of Dental Research, March 1986; 65(3): pages 417-420; K. C. Y. Tay et al., Journal of Endodontics, vol. 33, Issue 12, December 2007, pages 1438-1443). An apparatus identical to that used in the method of Pashley et al. was prepared, and the disc of bovine tooth having undergone the above dentinal tubule occlusion treatment was placed and fixed in a chamber jig capable of separation such that a liquid would permeate the disc of bovine tooth in the direction from dental pulp to enamel. The area of the dentin surface to be subjected to the pressure of a phosphate-buffered saline (Dulbecco's PBS, manufactured by Grand Island Biological Company, Grand Island, N.Y.) was limited to 78.5 mm$^2$ (diameter=5 mm) by an O-ring. A pressure of 15 cm $H_2O$, which is close to the pressure of the dentinal intratubular fluid, was applied to the dentin surface and, after 15 minutes, the amount of permeation was measured. The measurement of the amount of permeation was performed in the same manner as above also before the disc of bovine tooth was subjected to the dentinal tubule occlusion treatment. The dentin permeability reduction ratio (initial value) was calculated from the measurement results using the following equation.

Dentin permeability reduction ratio(initial value) (%)=[1−{(Amount of permeation measured for disc of bovine tooth after dentinal tubule occlusion)/(Amount of permeation measured for disc of bovine tooth before dentinal tubule occlusion)}]×100

(6) Dentin Permeability Reduction Ratio (Post-Acid Immersion Value)

The amount of permeation was measured using the same test method as that used for the above measurement of the dentin permeability reduction ratio (initial value), except for using the acid-immersed disc of bovine tooth instead of the disc of bovine tooth as subjected to the dentinal tubule occlusion treatment. The dentin permeability reduction ratio (post-acid immersion value) was calculated from the measurement results using the following equation.

Dentin permeability reduction ratio (post-acid immersion value) (%)=[1−{(Amount of permeation measured for disc of bovine tooth after acid immersion)/(Amount of permeation measured for disc of bovine tooth before dentinal tubule occlusion)}]×100

(7) Decrease in Dentin Permeability Reduction Ratio Caused by Acid Immersion

The values shown in the tables below for the decrease in dentin permeability reduction ratio caused by acid immersion were calculated by the following equation.

Decrease in dentin permeability reduction ratio caused by acid immersion (%)=100−{[Dentin permeability reduction ratio (post-acid immersion value)/Dentin permeability reduction ratio (initial value)]×100}

TABLE 1

| | Raw materials | | Example No. | | | | | | | | | |
|---|---|---|---|---|---|---|---|---|---|---|---|---|
| | | | 1 | 2 | 3 | 4 | 5 | 6 | 7 | 8 | 9 | 10 |
| Fluorapatite particles (A) | Fluorapatite (D50: 0.6 μm) | | | | | | | | | | | |
| | Fluorapatite (D50: 1.1 μm) | | | | | | | | | | | |
| | Fluorapatite (D50: 2.4 μm) | | 25.0 | 35.0 | 42.0 | 46.0 | 48.0 | 48.5 | 49.0 | 21.0 | 15.8 | 10.0 |
| | Fluorapatite (D50: 7.8 μm) | | | | | | | | | | | |
| Inorganic particles (B) that form Hap | b1 | TTCP (D50: 2.0 μm) | 12.5 | 7.5 | 4.0 | 2.0 | 1.0 | 0.75 | 0.5 | 2.0 | 1.5 | 1.0 |
| | b2 | DCPA (D50: 0.6 μm) | | | | | | | | | | |
| | b2 | DCPA (D50: 1.2 μm) | | | | | | | | | | |
| | b2 | DCPA (D50: 2.0 μm) | 12.5 | 7.5 | 4.0 | 2.0 | 1.0 | 0.75 | 0.5 | 2.0 | 1.5 | 1.0 |
| | b2 | DCPA (D50: 6.5 μm) | | | | | | | | | | |
| | b2 | α-TCP (D50: 2.0 μm) | | | | | | | | | | |
| | b3 | Calcium carbonate (D50: 2.4 μm) | | | | | | | | | | |
| | b3 | Calcium hydroxide (D50: 2.1 μm) | | | | | | | | | | |
| Fluorine compound | NaF | | | | | | | | | | | |
| Thickener | Ar-380 | | | | | | | | | | | |
| Dispersant (C) | MACROGOL 400 | | 10.0 | 10.0 | 10.0 | 10.0 | 10.0 | 10.0 | 10.0 | 20.0 | 19.0 | 20.0 |
| | MACROGOL 4000 | | 10.0 | 10.0 | 10.0 | 10.0 | 10.0 | 10.0 | 10.0 | 20.0 | 22.0 | 28.0 |
| | Glycerin | | 30.0 | 30.0 | 30.0 | 30.0 | 30.0 | 30.0 | 30.0 | 35.0 | 40.2 | 40.0 |
| Total | | | 100.0 | 100.0 | 100.0 | 100.0 | 100.0 | 100.0 | 100.0 | 100.0 | 100.0 | 100.0 |
| A/B (weight ratio) | | | 1.0 | 2.3 | 5.3 | 11.5 | 24.0 | 32.3 | 49.0 | 5.3 | 5.3 | 5.0 |
| Amount (parts by weight) of (C) relative to 100 parts by weight of (A) + (B) | | | 100.0 | 100.0 | 100.0 | 100.0 | 100.0 | 100.0 | 100.0 | 300.0 | 431.9 | 733.3 |
| Ca/P ratio (b1 + b2 or b2 + b3) | | | 1.43 | 1.43 | 1.43 | 1.43 | 1.43 | 1.43 | 1.43 | 1.43 | 1.43 | 1.43 |
| Ca/P ratio (b1 + b2 + b3) | | | — | — | — | — | — | — | — | — | — | — |
| Handling properties | | | A | A | A | A | A | A | A | A | A | A |
| Dentin permeability reduction ratio (initial value) (%) | | | 95.4 | 96.4 | 96.8 | 94.3 | 91.9 | 87.4 | 83.5 | 90.9 | 87.6 | 83.7 |
| Dentin permeability reduction ratio (post-acid immersion value) (%) | | | 85.9 | 88.4 | 91.3 | 90.7 | 89.5 | 84.5 | 80.5 | 85.6 | 82.4 | 79.3 |
| Decrease in dentin permeability reduction ratio (%) | | | 10.0 | 8.3 | 5.7 | 3.8 | 2.6 | 3.3 | 3.6 | 5.8 | 5.9 | 5.3 |
| Storage stability | | | Good | Good | Good | Good | Good | Good | Good | Good | Good | Good |

TABLE 1-continued

| | Raw materials | | Example No. 11 | 12 | 13 | 14 |
|---|---|---|---|---|---|---|
| Fluorapatite particles (A) | | Fluorapatite (D50: 0.6 μm) | | | | |
| | | Fluorapatite (D50: 1.1 μm) | | | | |
| | | Fluorapatite (D50: 2.4 μm) | 9.0 | 63.0 | 66.0 | 42.0 |
| | | Fluorapatite (D50: 7.8 μm) | | | | |
| Inorganic particles (B) that form Hap | b1 | TTCP (D50: 2.0 μm) | 0.9 | 6.3 | 6.6 | 4.0 |
| | b2 | DCPA (D50: 0.6 μm) | | | | |
| | b2 | DCPA (D50: 1.2 μm) | | | | |
| | b2 | DCPA (D50: 2.0 μm) | 0.9 | 6.3 | 6.6 | |
| | b2 | DCPA (D50: 6.5 μm) | | | | |
| | b2 | α-TCP (D50: 2.0 μm) | | | | 4.0 |
| | b3 | Calcium carbonate (D50: 2.4 μm) | | | | |
| | b3 | Calcium hydroxide (D50: 2.1 μm) | | | | |
| Fluorine compound | | NaF | | | | |
| Thickener | | Ar-380 | | | | |
| Dispersant (C) | | MACROGOL 400 | 20.0 | 4.0 | 4.0 | 10.0 |
| | | MACROGOL 4000 | 28.0 | 0.0 | 0.0 | 10.0 |
| | | Glycerin | 41.2 | 20.4 | 16.8 | 30.0 |
| Total | | | 100.0 | 100.0 | 100.0 | 100.0 |
| A/B (weight ratio) | | | 5.0 | 5.0 | 5.0 | 5.3 |
| Amount (parts by weight) of (C) relative to 100 parts by weight of (A) + (B) | | | 825.9 | 32.3 | 26.3 | 100.0 |
| Ca/P ratio (b1 + b2 or b2 + b3) | | | 1.43 | 1.43 | 1.43 | 1.73 |
| Ca/P ratio (b1 + b2 + b3) | | | — | — | — | — |
| Handling properties | | | A | B | B | A |
| Dentin permeability reduction ratio (initial value) (%) | | | 81.8 | 97.8 | 90.8 | 93.8 |
| Dentin permeability reduction ratio (post-acid immersion value) (%) | | | 77.4 | 94.2 | 85.4 | 88.3 |
| Decrease in dentin permeability reduction ratio (%) | | | 5.4 | 3.7 | 5.9 | 5.9 |
| Storage stability | | | Good | Good | Good | Good |

TABLE 2

| | Raw materials | | Example No. 15 | 16 | 17 | 18 | 19 | 20 | 21 | 22 | 23 | 24 |
|---|---|---|---|---|---|---|---|---|---|---|---|---|
| Fluorapatite particles (A) | Fluorapatite (D50: 0.6 μm) | | | | | | | 46.0 | | | | |
| | Fluorapatite (D50: 1.1 μm) | | | | | | | | 46.0 | | | |
| | Fluorapatite (D50: 2.4 μm) | | 42.0 | 42.0 | 42.0 | 42.0 | 42.0 | | | | 46.0 | 46.0 |
| | Fluorapatite (D50: 7.8 μm) | | | | | | | | | 46.0 | | |
| Inorganic particles (B) that form Hap | b1 | TTCP (D50: 2.0 μm) | | | 3.0 | 2.0 | 1.5 | 2.0 | 2.0 | 2.0 | 2.0 | 2.0 |
| | b2 | DCPA (D50: 0.6 μm) | | | | | | | | | 2.0 | |
| | b2 | DCPA (D50:1.2 μm) | | | | | | | | | | 2.0 |

TABLE 2-continued

|  |  | Raw materials |  |  |  |  |  |  |  |  |  |  |
|---|---|---|---|---|---|---|---|---|---|---|---|---|
|  | b2 | DCPA (D50: 2.0 μm) | 6.0 | 6.0 | 2.5 | 2.0 | 5.0 | 2.0 | 2.0 | 2.0 |  |  |
|  | b2 | DCPA (D50: 6.5 μm) |  |  |  |  |  |  |  |  |  |  |
|  | b2 | α-TCP (D50: 2.0 μm) |  |  |  |  |  |  |  |  |  |  |
|  | b3 | Calcium carbonate (D50: 2.4 μm) | 2.0 |  | 2.5 | 4.0 | 1.5 |  |  |  |  |  |
|  | b3 | Calcium hydroxide (D50: 2.1 μm) |  | 2.0 |  |  |  |  |  |  |  |  |
| Fluorine compound |  | NaF |  |  |  |  |  |  |  |  |  |  |
| Thickener |  | Ar-380 |  |  |  |  |  |  |  |  |  |  |
| Dispersant (C) |  | MACROGOL 400 | 10.0 | 10.0 | 10.0 | 10.0 | 10.0 | 10.0 | 10.0 | 10.0 | 10.0 | 10.0 |
|  |  | MACROGOL 4000 | 10.0 | 10.0 | 10.0 | 10.0 | 10.0 | 10.0 | 10.0 | 10.0 | 10.0 | 10.0 |
|  |  | Glycerin | 30.0 | 30.0 | 30.0 | 30.0 | 30.0 | 30.0 | 30.0 | 30.0 | 30.0 | 30.0 |
| Total |  |  | 100.0 | 100.0 | 100.0 | 100.0 | 100.0 | 100.0 | 100.0 | 100.0 | 100.0 | 100.0 |
| A/B (weight ratio) |  |  | 5.3 | 5.3 | 5.3 | 5.3 | 5.3 | 11.5 | 11.5 | 11.5 | 11.5 | 11.5 |
| Amount (parts by weight) of (C) relative to 100 parts by weight of (A) + (B) |  |  | 100.0 | 100.0 | 100.0 | 100.0 | 100.0 | 100.0 | 100.0 | 100.0 | 100.0 | 100.0 |
| Ca/P ratio (b1 + b2 or b2 + b3) |  |  | 1.45 | 1.61 | — | — | — | 1.43 | 1.43 | 1.43 | 1.43 | 1.43 |
| Ca/P ratio (b1 + b2 + b3) |  |  | — | — | 2.20 | 2.98 | 1.52 | — | — | — | — | — |
| Handling properties |  |  | A | A | A | A | A | A | A | A | A | A |
| Dentin permeability reduction ratio (initial value) (%) |  |  | 91.9 | 92.1 | 98.5 | 94.9 | 94.1 | 86.9 | 91.3 | 88.1 | 88.6 | 90.6 |
| Dentin permeability reduction ratio (post-acid immersion value) (%) |  |  | 86.1 | 85.2 | 96.5 | 90.3 | 89.8 | 80.7 | 87.5 | 84.7 | 83.6 | 87.2 |
| Decrease in dentin permeability reduction ratio (%) |  |  | 6.3 | 7.5 | 2.0 | 4.8 | 4.6 | 7.1 | 4.2 | 3.9 | 5.6 | 3.8 |
| Storage stability |  |  | Good | Good | Good | Good | Good | Good | Good | Good | Good | Good |

|  | Raw materials |  | Example No. 25 | Example No. 26 | Example No. 27 | Example No. 28 |
|---|---|---|---|---|---|---|
| Fluorapatite particles (A) | Fluorapatite (D50: 0.6 μm) |  |  |  |  |  |
|  | Fluorapatite (D50: 1.1 μm) |  |  |  |  |  |
|  | Fluorapatite (D50: 2.4 μm) |  | 46.0 | 42.0 | 42.0 | 46.0 |
|  | Fluorapatite (D50: 7.8 μm) |  |  |  |  |  |
| Inorganic particles (B) that form Hap | b1 | TTCP (D50: 2.0 μm) | 2.0 | 7.5 | 2.7 | 2.0 |
|  | b2 | DCPA (D50: 0.6 μm) |  |  |  |  |
|  | b2 | DCPA (D50:1.2 μm) | 2.0 |  |  |  |
|  | b2 | DCPA (D50: 2.0 μm) |  | 0.5 | 5.3 | 2.0 |
|  | b2 | DCPA (D50: 6.5 μm) | 2.0 |  |  |  |
|  | b2 | α-TCP (D50: 2.0 μm) |  |  |  |  |
|  | b3 | Calcium carbonate (D50: 2.4 μm) |  |  |  |  |
|  | b3 | Calcium hydroxide (D50: 2.1 μm) |  |  |  |  |
| Fluorine compound | NaF |  |  |  |  | 0.3 |
| Thickener | Ar-380 |  |  |  |  | 5.0 |
| Dispersant (C) | MACROGOL 400 |  | 10.0 | 10.0 | 10.0 | 10.0 |
|  | MACROGOL 4000 |  | 10.0 | 10.0 | 10.0 | 4.7 |
|  | Glycerin |  | 30.0 | 30.0 | 30.0 | 30.0 |
| Total |  |  | 100.0 | 100.0 | 100.0 | 100.0 |
| A/B (weight ratio) |  |  | 11.5 | 5.3 | 5.3 | 11.5 |
| Amount (parts by weight) of (C) relative to 100 parts by weight of (A) + (B) |  |  | 100.0 | 100.0 | 100.0 | 89.4 |
| Ca/P ratio (b1 + b2 or b2 + b3) |  |  | 1.43 | 1.91 | 1.26 | 1.43 |
| Ca/P ratio (b1 + b2 + b3) |  |  | — | — | — | — |
| Handling properties |  |  | A | A | A | A |

TABLE 2-continued

|  |  |  |  |  |
|---|---|---|---|---|
| Dentin permeability reduction ratio (initial value) (%) | 91.8 | 91.7 | 90.9 | 97.2 |
| Dentin permeability reduction ratio (post-acid immersion value) (%) | 87.5 | 86.1 | 84.9 | 94.8 |
| Decrease in dentin permeability reduction ratio (%) | 4.7 | 6.1 | 6.6 | 2.5 |
| Storage stability | Good | Good | Good | Good |

TABLE 3

| Raw materials | | Example No. 29 | 30 | 31 | 32 |
|---|---|---|---|---|---|
| Fluorapatite particles (A) | Fluorapatite (D50: 0.6 μm) | | | | |
|  | Fluorapatite (D50: 1.1 μm) | | | | |
|  | Fluorapatite (D50: 2.4 μm) | 25.0 | 42.0 | 42.0 | 42.0 |
|  | Fluorapatite (D50: 7.8 μm) | | | | |
| Inorganic particles (B) that form Hap | b1 TTCP (D50: 2.0 μm) | 12.5 | 4.0 | | |
|  | b2 DCPA (D50: 0.6 μm) | | | | |
|  | b2 DCPA (D50: 1.2 μm) | | | | |
|  | b2 DCPA (D50: 2.0 μm) | | | 6.0 | 5.0 |
|  | b2 DCPA (D50: 6.5 μm) | | | | |
|  | b2 α-TCP (D50: 2.0 μm) | | | | |
|  | b2 DCPD (D50: 2.3 μm) | 12.5 | | | |
|  | b2 β-TCP (D50: 2.5 μm) | | 4.0 | | |
|  | b3 Calcium carbonate (D50: 2.4 μm) | | | | |
|  | b3 Calcium hydroxide (D50: 2.1 μm) | | | | |
|  | b3 Tricalcium silicate (D50: 1.9 μm) | | | 2.0 | |
|  | b3 Dicalcium silicate (D50: 2.5 μm) | | | | 3.0 |
| Fluorine compound | NaF | | | | |
| Thickener | Ar-380 | | | | |
| Dispersant (c) | MACROGOL 400 | 10.0 | 10.0 | 10.0 | 10.0 |
|  | MACROGOL 4000 | 10.0 | 10.0 | 10.0 | 10.0 |
|  | Glycerin | 30.0 | 30.0 | 30.0 | 30.0 |
| Total | | 100.0 | 100.0 | 100.0 | 100.0 |
| A/B (weight ratio) | | 1.0 | 5.3 | 5.3 | 5.3 |
| Amount (parts by weight) of (C) relative to 100 parts by weight of (A) + (B) | | 100.0 | 100.0 | 100.0 | 100.0 |
| Ca/P ratio (b1 + b2 or b2 + b3) | | 1.48 | 1.73 | 1.60 | 1.46 |
| Ca/P ratio (b1 + b2 + b3) | | — | — | — | — |
| Handling properties | | A | A | A | A |
| Dentin permeability reduction ratio (initial value) (%) | | 94.1 | 92.8 | 92.1 | 92.3 |
| Dentin permeability reduction ratio (post-acid immersion value) (%) | | 86.2 | 86.9 | 85.0 | 84.8 |
| Decrease in dentin permeability reduction ratio (%) | | 8.4 | 6.4 | 7.7 | 8.1 |
| Storage stability | | Good | Good | Good | Good |

TABLE 4

| Raw materials | | Comparative Example No. 1 | 2 | 3 | 4 | 5 | 6 | 7 | 8 | 9 |
|---|---|---|---|---|---|---|---|---|---|---|
| Fluorapatite particles (A) | Fluorapatite (D50: 2.4 μm) | | | 46.0 | 46.0 | 46.0 | | | | |
| Fluorapatite particles (A') | Fluorapatite (D50: 0.2 μm) | 46.0 | | | | | | | | |
|  | Fluorapatite (D50: 20.4 μm) | | 46.0 | | | | | | | |
| Hydroxyapatite particles | Hydroxyapatite (D50: 150 nm) | | | | | | | | 50.0 | |
| Inorganic particles (B) that form Hap | b1 TTCP (D50: 2.0 μm) | 2.0 | 2.0 | | | | | | 36.0 | |
|  | b2 DCPA (D50: 2.0 μm) | 2.0 | 2.0 | | | | | | 13.6 | 55.0 |
|  | b2 α-TCP (D50: 2.0 μm) | | | | | | 50.00 | | | |
|  | b3 Calcium hydroxide (D50: 2.1 μm) | | | | | | | | | 0.5 |

TABLE 4-continued

| Raw materials | | | 1 | 2 | 3 | 4 | 5 | 6 | 7 | 8 | 9 |
|---|---|---|---|---|---|---|---|---|---|---|---|
| Inorganic particles (B') that form Hap | b1' | TTCP (D50: 20.4 μm) | | | 2.0 | | 1.5 | | | | |
| | b2' | DCPA (D50: 20.8 μm) | | | 2.0 | 3.0 | 1.3 | | | | |
| | b3' | Calcium hydroxide (D50: 14.5 μm) | | | | 1.0 | 1.2 | | | | |
| Alkali metal phosphate | | $Na_2HPO_4$ (D50: 5.2 μm) | | | | | | | | 4.9 | 10 |
| Water | | Water | | | | | | | | 45.5 | 35 |
| Dispersant (C') | | MACROGOL 400 | 10.0 | 10.0 | 10.0 | 10.0 | 10.0 | 10.0 | 10.0 | | |
| | | MACROGOL 4000 | 10.0 | 10.0 | 10.0 | 10.0 | 10.0 | 10.0 | 10.0 | | |
| | | Glycerin | 30.0 | 30.0 | 30.0 | 30.0 | 30.0 | 30.0 | 30.0 | | |
| Total | | | 100.0 | 100.0 | 100.0 | 100.0 | 100.0 | 100.0 | 100.0 | 100.0 | 100.0 |
| Fluorapatite particles/inorganic particles (weight ratio) | | | 0.0 | 0.0 | 11.5 | 11.5 | 11.5 | — | — | — | — |
| Amount (parts by weight) of (C) relative to 100 parts by weight of fluorapatite particles + inorganic particles | | | 100.0 | 100.0 | 100.0 | 100.0 | 100.0 | — | — | — | — |
| Ca/P ratio (b1 + b2 or b2 + b3) | | | 1.43 | 1.43 | 1.43 | 1.61 | — | — | — | — | — |
| Ca/P ratio (b1 + b2 + b3) | | | — | — | — | — | 2.20 | — | — | — | — |
| Handling properties | | | A | A | A | A | A | A | A | A | A |
| Dentin permeability reduction ratio(initial value) (%) | | | 50.5 | 32.1 | 69.3 | 67.4 | 68.5 | 64.3 | 66.8 | 98.7 | 94.2 |
| Dentin permeability reduction ratio (post-acid immersion value) (%) | | | 38.5 | 21.6 | 67.2 | 64.7 | 65.8 | 30.2 | 43.2 | 61.2 | 48.2 |
| Decrease in dentin permeability reduction ratio (%) | | | 23.8 | 32.7 | 3.0 | 4.0 | 3.9 | 53.0 | 35.3 | 38.0 | 48.8 |
| Storage stability | | | Good | Good | Good | Good | Good | Good | Good | Poor | Poor |

As shown in Table 4, for the dentinal tubule occlusion materials of Comparative Examples 1 to 7, the initial value of the dentin permeability reduction ratio was 69.3% or less, and the post-acid immersion value of the dentin permeability reduction ratio was 67.2% or less. In particular, in Comparative Examples 1, 2, 6, and 7, the decrease in dentin permeability reduction ratio caused by acid immersion was 23.8% or more, which means that the resistance of dentinal tubule occlusion to acids was low. The dentinal tubule occlusion materials of Comparative Examples 8 and 9 had low storage stability. Furthermore, the post-acid immersion value of the dentin permeability reduction ratio was 61.2% in Comparative Example 8 and 48.2% in Comparative Example 9, and the decrease in dentin permeability reduction ratio caused by acid immersion was 38.0% in Comparative Example 8 and 48.8% in Comparative Example 9, which means that the resistance of dentinal tubule occlusion to acids was low.

By contrast, for the one-pack type dentinal tubule occlusion materials of the present invention, the initial value of the dentin permeability reduction ratio was 81.8% or more. Furthermore, for the one-pack type dentinal tubule occlusion materials of the present invention, the post-acid immersion value of the dentin permeability reduction ratio was 77.4% or more, and the decrease in dentin permeability reduction ratio caused by acid immersion was 10.0% or less, despite the fact that any alkali metal phosphate such as those in Comparative Examples 8 and 9 was not used. It was also confirmed that the one-pack type dentinal tubule occlusion materials of the present invention were excellent in terms of handling properties and storage stability.

INDUSTRIAL APPLICABILITY

The non-aqueous dentinal tubule occlusion material of the present invention is excellent in terms of initial degree of dentinal tubule occlusion, resistance of dentinal tubule occlusion to acids, handling properties, and storage stability. The dentinal tubule occlusion material of the present invention is an one-pack type material, which eliminates the need for the practitioner to perform material preparation each time he/she uses the material. Furthermore, the dentinal tubule occlusion material of the present invention is capable of achieving secure occlusion of dentinal tubules and is therefore useful for treatment of dentinal hypersensitivity.

The invention claimed is:

1. A one-pack type non-aqueous dentinal tubule occlusion material, comprising:
    fluorapatite particles (A) having an average particle diameter of 1.5 to 10 μm;
    inorganic particles (B) having an average particle diameter of 0.6 to 10 μm and reactive with water to form apatite; and
    a non-aqueous dispersant (C),
    wherein
    (i) the inorganic particles (B) comprise a mixture of basic calcium phosphate particles (b1) and poorly-soluble calcium phosphate particles (b2), or
    (ii) a mixture of the poorly-soluble calcium phosphate particles (b2) and a phosphorus-free calcium compound (b3), or
    (iii) the inorganic particles (B) comprise a mixture of basic calcium phosphate particles (b1), poorly-soluble calcium phosphate particles (b2), and a phosphorus-free calcium compound (b3),
    and wherein
    a Ca/P ratio in a total of the particles (b1) and the particles (b2) or in a total of the particles (b2) and the compound (b3) in the (i) or (ii) is 1.2 to 2.0, or
    a Ca/P ratio in a total of the particles (b1), the particles (b2), and the compound (b3) in the (iii) is 1.5 to 3.0.

2. The non-aqueous dentinal tubule occlusion material according to claim 1, wherein a weight ratio (A/B) of the fluorapatite particles (A) to the inorganic particles (B) is 0.1 to 50.

3. The non-aqueous dentinal tubule occlusion material according to claim 1, wherein the non-aqueous dispersant (C) is comprised in an amount of 25 to 900 parts by weight relative to 100 parts by weight of a total of the fluorapatite particles (A) and the inorganic particles (B).

4. The non-aqueous dentinal tubule occlusion material according to claim 1, wherein the non-aqueous dispersant (C) is at least one selected from the group consisting of a polyether, a monohydric alcohol, and a polyhydric alcohol.

5. The non-aqueous dentinal tubule occlusion material according to claim 4, wherein
- the basic calcium phosphate particles (b1) are at least one selected from the group consisting of tetracalcium phosphate and octacalcium phosphate pentahydrate,
- the poorly-soluble calcium phosphate particles (b2) are at least one selected from the group consisting of dibasic calcium phosphate anhydrous, tricalcium phosphate, monobasic calcium phosphate anhydrous, amorphous calcium phosphate, calcium acid pyrophosphate, dibasic calcium phosphate dihydrate, and monobasic calcium phosphate monohydrate, and
- the phosphorus-free calcium compound (b3) is at least one selected from the group consisting of calcium hydroxide, calcium oxide, calcium chloride, calcium nitrate, calcium acetate, calcium lactate, calcium citrate, calcium metasilicate, dicalcium silicate, tricalcium silicate, and calcium carbonate.

* * * * *

UNITED STATES PATENT AND TRADEMARK OFFICE
CERTIFICATE OF CORRECTION

PATENT NO. : 10,603,250 B2
APPLICATION NO. : 15/522434
DATED : March 31, 2020
INVENTOR(S) : Kenji Hatanaka et al.

Page 1 of 1

It is certified that error appears in the above-identified patent and that said Letters Patent is hereby corrected as shown below:

On the Title Page

Item (73), the Assignee's city of record is incorrect. Item (73) should read:
-- (73) Assignee: KURARAY NORITAKE DENTAL INC., Kurashiki-shi (JP) --

Signed and Sealed this
Nineteenth Day of May, 2020

Andrei Iancu
*Director of the United States Patent and Trademark Office*